United States Patent [19]

Lee

[11] Patent Number: 5,645,069

[45] Date of Patent: Jul. 8, 1997

[54] SYSTEM FOR AND METHOD OF ANALYZING ELECTROCARDIOGRAMS EMPLOYING CHAOS TECHNIQUES

[75] Inventor: Ki Hak Lee, Seoul, Rep. of Korea

[73] Assignee: LG Electronics Inc., Seoul, Rep. of Korea

[21] Appl. No.: 448,993

[22] Filed: May 24, 1995

[30] Foreign Application Priority Data

May 26, 1994 [KR] Rep. of Korea ............... 11520/1994
Dec. 1, 1994 [KR] Rep. of Korea ............... 32469/1994

[51] Int. Cl.$^6$ .................................................. A61B 5/0402
[52] U.S. Cl. ........................... 128/702; 128/696; 128/705; 128/706
[58] Field of Search .................................. 128/702, 705, 128/706, 696, 699; 364/413.06

[56] References Cited

U.S. PATENT DOCUMENTS

5,201,321  4/1993  Fulton ............................ 128/702
5,285,793  2/1994  Slovut et al. ..................... 128/706

*Primary Examiner*—William E. Kamm
*Assistant Examiner*—Kennedy J. Schaetzle

[57] ABSTRACT

A system and method for analyzing an electrocardiogram (ECG) acquires ECG time series data from an examinee's ECG signal in a real time, subjects the acquired ECG time series data to a base line filtering, reconstructs an ECG attractor on the basis of the base line-filtered time series data by use of qualitative and quantitative analysis methods, and derives a correlation dimension value on the basis of the reconstructed ECG attractor, whereby the examinee's health and psychological conditions can be accurately diagnosed on the basis of the reconstructed attractor and correlation dimension value.

16 Claims, 7 Drawing Sheets

SYSTEM FOR AND METHOD OF ANALYZING ELECTROCARDIOGRAMS EMPLOYING CHAOS TECHNIQUES

BACKGROUND OF THE INVENTION

1. Field of the Invention

The present invention relates to a system for and a method of analyzing an electrocardiogram (ECG), and more particularly to a system for and a method of analyzing an ECG, capable of analyzing an ECG signal generated by the pulsation of the heart in a chaotic fashion using an attractor reconstruction which is one of qualitative analysis methods and using a correlation dimension which is one of quantitative analysis methods.

2. Description of the Prior Art

ECG signals generated by the pulsation of the heart can be interpreted by the chaos theory. Chaos systems which are analyzing systems utilizing the chaos theory belong to the category of nonlinear deterministic dynamic systems. Here, the "dynamic system" means the system wherein its system controlling state varies by the lapse of time. The "deterministic system" means the system wherein its system state after a given time elapses can be accurately determined in so far as a state variable controlling the dynamic system and a current initial condition are known. Such nonlinear deterministic dynamic systems are divided into four classes, namely, the equilibrium point system, the periodic of limit cycle system, the quasi-periodic or torus system, and the chaos system. As compared to other systems, the chaos system disables a prediction of the future because it is very sensitive to the initial condition, in spite of the deterministic presence thereof. The chaos system has important features, that is, an infinite cycle thereof (no presence of any cycle) and a state variation very sensitive to the initial condition. Methods for analyzing and establishing chaos phenomena occurring in nature are classified into the qualitative analysis method based on the topology of attractor and the quantitative analysis method based on the dimension. Such a classification is based on the fact that a specified chaos system has an intrinsic attractor topology and an intrinsic dimension.

The qualitative analysis method is to analyze a specified system using a path along which the trajectory of a state variation moves by the lapse of time and the topology of the whole trajectory. As described above, chaos systems are nonlinear deterministic dynamic systems. Information essentially required in a dynamic system to indicate how the system varies by the lapse of time is referred to as "state". The equation expressing the state of a chaos system, that is, the state equation has the form of a differential equation or the form of a difference equation. A variation in state occurring after a given time lapses under a condition that an initial condition has been given is referred to as the solution of a state equation or the trajectory on a state plane. The point on which the trajectory converges. "Attractor construction" is to derive the solution of the state equation of a specified chaos system and to indicate the derived solution in a state space. In other words, the attractor may be referred to as a graphic method for indicating acts and characteristics of a specified system in a state space. Where an attractor construction is carried out in a two-dimensional state space, a value X of the state occurring after a given time lapses is indicated on an X-axis of the state space. At the same time, a differential value X' of the state value indicated on the X-axis is indicated on an Y-axis of the state space. It is impossible to find all state variables and parameters of a specified chaos system existing in the nature and derive a state equation of the system. Takens verified that where a variation in one of the state variables importantly affecting the system is experimentally measured in the form of time series data and a reconstruction of attractor is carried out based on the measured time series data, the reconstructed attractor has a similar topology to the original attractor. The reconstruction of attractor is achieved using sampled time series data, embedding dimension and delay time.

Where m-dimensional vectors are constructed from time series data $\{X_1, X_2, X_3, \ldots, X_N\}$ (here, N is a sufficiently large value) detected for an attractor reconstruction, they are expressed as follows:

$$Y_i = \{X_i, X_{i+p}, X_{i+2p}, X_{i+3p}, \ldots, X_{i+(m-1)p}\}$$

where, $i = 0, 1, 2, 3, \ldots, N$

Using the embedding dimension m and the delay time p, the reconstructed time series data are derived as follows:

$$\{X_1, X_2, X_3, \ldots, X_N\} \rightarrow \{X(t), X(t+p), X(t+2p), X(t+3p), \ldots, X(t+(m-1)p)\}$$

where, t represents the time of the reconstructed time series data.

Figure 1:
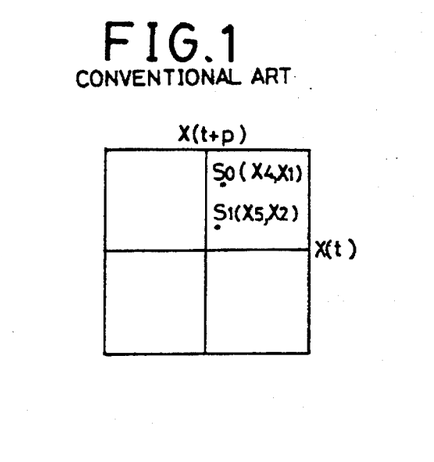
FIG. 1 is a schematic view explaining an attractor reconstructing method.
Figure 2A:
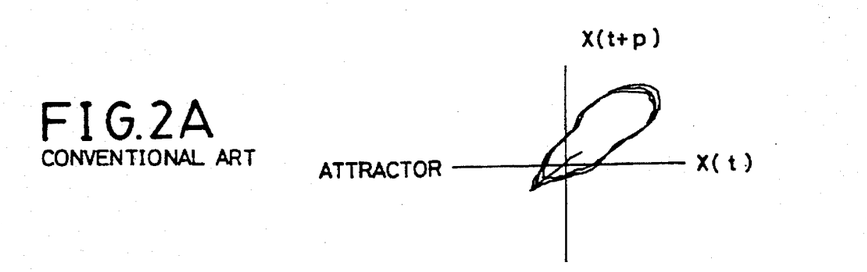
FIGS. 2A to 2C are diagrams respectively showing various characteristics of an ECG chaos system, namely, a reconstructed attractor, time series data and a frequency characteristic.
Figure 2B:
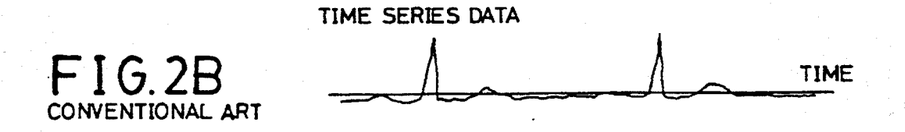
Figure 2C:
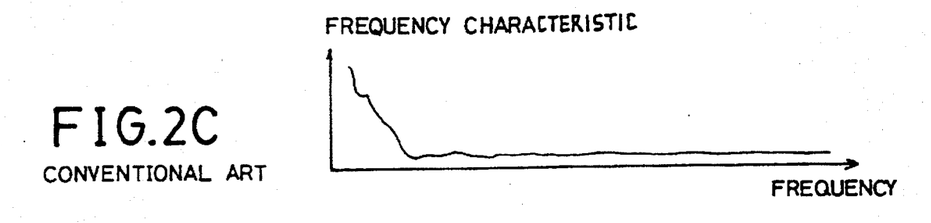

The reconstruction of time series data is carried out in a two-dimensional plane when the embedding dimension m is 2 and in a three-dimensional space when the embedding dimension m is 3. However, time series data are reconstructed generally in two-dimensional planes. For example, where the embedding dimension m and the delay time p are 2 and 3, respectively, the following vectors are reconstructed from time series data $\{X_1, X_2, X_3, \ldots, X_N\}$ measured:

$S_0 = \{X_4, X_1\}$
$S_0 = \{X_5, X_2\}$
$S_0 = \{X_6, X_3\}$
$S_0 = \{X_7, X_4\} \ldots$
$S_{N-4} = \{X_N, X_{N-3}\}$ Each of the reconstructed vectors has two vector components one being associated with an X-axis while the other being associated with a Y-axis. As $S_0, S_1, S_2, \ldots, S_{N-3}$ are sequentially plotted in a two-dimensional state space, reconstruction of the attractor of the specified chaos system is achieved. In other words, the plotted results indicate the reconstructed attractor. FIG. 1 illustrates the case wherein vectors $S_0$ and $S_1$ are plotted in a two-dimensional state space. Such an attractor reconstruction can be meaningful only when the delay time for the attractor reconstruction is appropriate. If the delay time is excessively small, the reconstructed attractor has a topology shaped into a diagonal line because of $X(0) \cong X(P) \cong X(2P)$. In the case of an excessively large delay time, the association between $X(0)$ and $X(P)$ disappears due to noise. As a result, the attractor reconstruction is meaningless. It, therefore, is very important to select an appropriate delay time. Generally, such a delay time is known to be a quarter of the basic cycle of a dynamic system and may be derived using an autocorrelation function. FIGS. 2A to 2C illustrate a reconstructed attractor, time series data and a frequency characteristic of an ECG chaos system, respectively.

The correlation dimension which is one of quantitative analysis methods for chaos systems will now be described. The reason why the correlation dimension is important in analyzing chaos systems is because a specified chaos system has an intrinsic correlation dimension value that we can not explain theoretically, but easily derive from experimental data based on the embedding dimension and delay time used to reconstruct a state space. For deriving such a correlation dimension value, m-dimensional vectors are first constructed from time series data as follows:

$Y_1 = \{X_1, X_{1+p}, X_{1+2p}, X_{1+3p}, \ldots, X_{1+(m-1)p}\}$
$Y_2 = \{X_2, X_{2+p}, X_{2+2p}, X_{2+3p}, \ldots, X_{2+(m-1)p}\}$
$Y_3 = \{X_3, X_{3+p}, X_{3+2p}, X_{3+3p}, \ldots, X_{3+(m-1)p}\} \ldots$
$Y_i = \{X_i, X_{i+p}, X_{i+2p}, X_{i+3p}, \ldots, X_{i+(m-1)p}\} \ldots$
$Y_j = \{X_j, X_{j+p}, X_{j+2p}, X_{j+3p}, \ldots, X_{j+(m-1)p}\} \ldots$
$Y_M = \{X_M, X_{M+p}, X_{M+2p}, X_{M+3p}, \ldots, X_{M+(m-1)p}\}$ where, m represents the embedding dimension, p represents the delay time, and M represents the number of vectors identical to the number of data N.

If two successive ones of the vectors derived as above have a distance $|Y_i - Y_j|$ less than a given, very small value $\epsilon$ therebetween, they are regarded as having a correlation.

Correlation sum or correlation integral $C(\epsilon)$ is expressed as follows:

$$C(\epsilon) = \frac{1}{M^2} \sum_{i=j}^{M} T(\epsilon - |Y_i - Y_j|)$$

Assuming that "$\epsilon - |Y_i - Y_j|$" in this equation is x, T(x) is 1 under a condition of x>0 (T(x)=1) and 0 under a condition of x<0 (T(x)=0). Accordingly, the correlation sum $C(\epsilon)$ is a step function serving as a counter.

The correlation dimension $D_c$ is defined as follows:

$$D_c = \sum_{\epsilon \to 0} \frac{\log C(\epsilon)}{\log \epsilon}$$

Figure 3A:
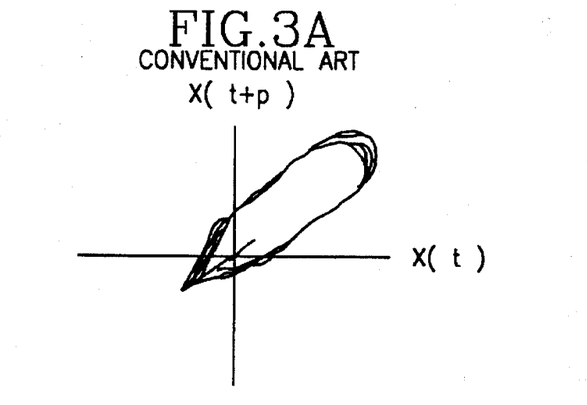
FIGS. 3A and 3B are diagrams respectively explaining a method for determining whether data from a specified chaos system is a chaos signal or a noise signal, using a correlation dimension value.
Figure 3B:
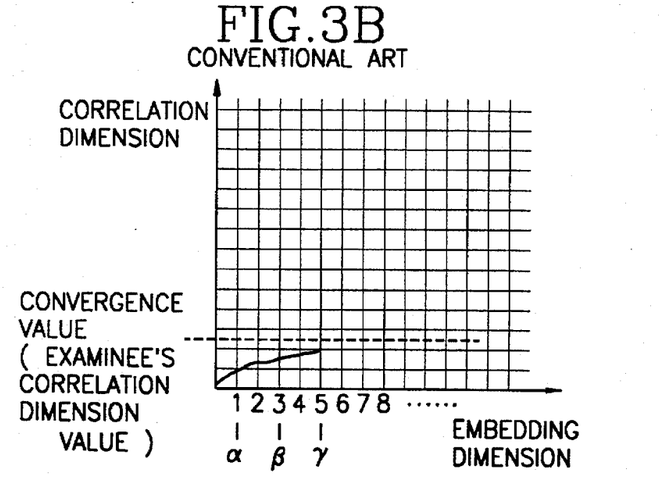
Figure 4A:
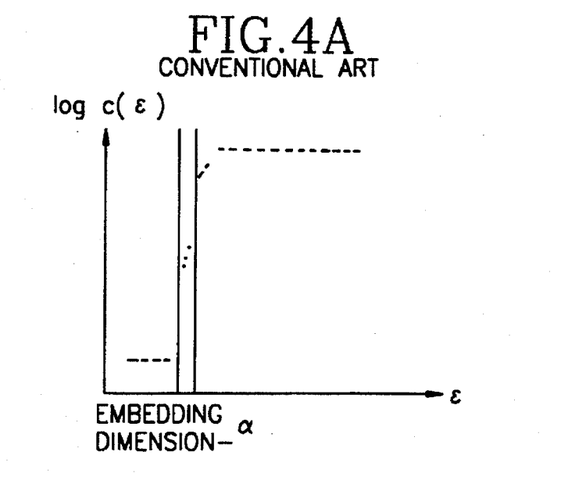
FIGS. 4A to 4C are diagrams respectively showing a method for deriving a correlation dimension value at an optional embedding dimension.
Figure 4B:
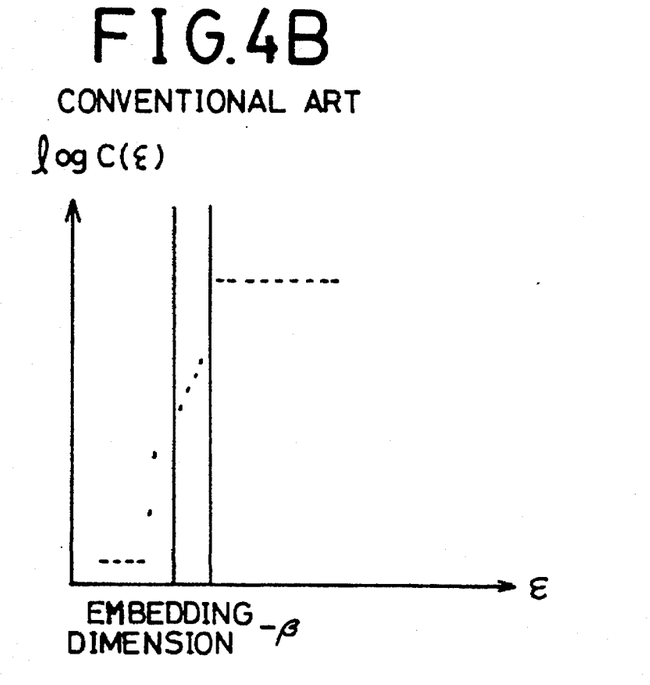
Figure 4C:
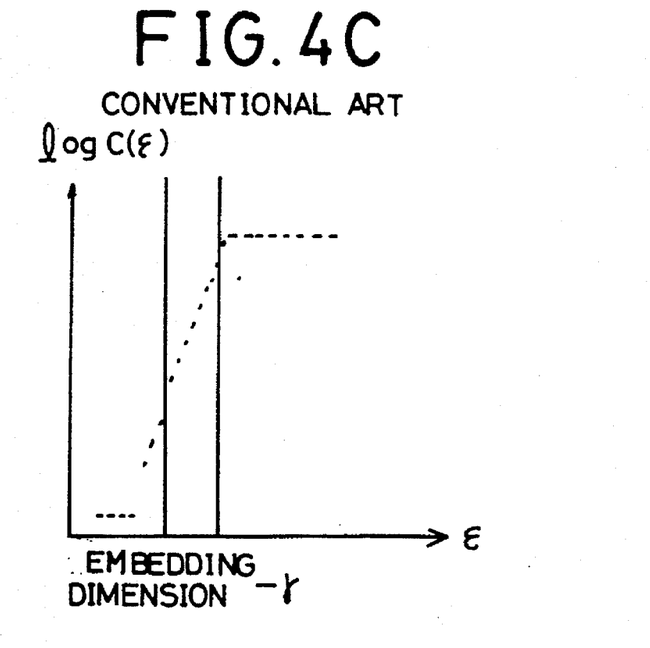

When $\epsilon$ is excessively large, all vectors are correlated together. In this case, the correlation sum $C(\epsilon)$ becomes 1, thereby causing the correlation dimension $D_c$ to be zero ($D_c=0$). In the case of $C(\epsilon) \propto \epsilon^v$, the correlation dimension $D_c$ corresponds to V with respect to $\epsilon$ which is variable. Since $\epsilon^v$ is effective only in the range of $\epsilon$ in which the correlation sum $C(\epsilon)$ has a linearity, it is very important to calculate the correlation dimension by finding a linear domain defined between two optional points on a log $C(\epsilon)$-to-log $\epsilon$ plot curve. However, there is a difficulty to experimentally calculate the correlation dimension. In other words, there is a possibility of experimental error because the linearity between two points on the log-log plot curve is indefinitely exhibited due to the presence of more or less noise signals in experimental data. It, therefore, is necessary to determine whether experimental data from a specified chaos system is a chaos signal or a meaningless noise signal. This determination can be accomplished using a correlation dimension graph for the chaos system. FIGS. 3A and 3B show a method for determining whether experimental data from a specified chaos system is a chaos signal or a meaningless noise signal, respectively. FIG. 3A shows an attractor reconstructed using an appropriate delay time. FIG. 3B shows a graph drawn by plotting a variation in the correlation dimension value of the reconstructed attractor shown in FIG. 3A upon varying the embedding dimension into $\alpha, \beta, \Gamma \ldots$, in this order. Where correlation dimension values plotted converge algebraically, their convergence value becomes the correlation dimension of the system. In this case, the experimental data is the chaos signal. On the contrary, where the correlation dimension values diverge, the experimental data is the noise signal. FIGS. 4A to 4C are diagrams respectively showing methods for deriving correlation dimension values at different embedding dimensions of $\alpha, \beta$ and $\Gamma$. Deriving an embedding dimension is the same as deriving the slope of the linearity-exhibited portion of an interval in which the value of log $C(\epsilon)$ varies. The correlation dimension has not integral dimensions, but has fractal dimensions. This feature of the correlation dimension is one of the important features of the chaos.

However, such a chaos theory has been hardly utilized to analyze ECG signals generated by the pulsation of the heart, in spite of the fact that ECG signals have chaotic features, namely, unique attractor topologies and correlation dimension values individually depending on the health and psychological conditions.

SUMMARY OF THE INVENTION

Therefore, an object of the invention is to provide a system for and a method of analyzing an ECG, capable of obtaining ECG time series data from an ECG signal in a real time, reconstructing an ECG attractor on the basis of the obtained time series data by use of qualitative and quantitative analysis methods, deriving a correlation dimension and thereby interpreting the ECG signal in a chaotic fashion.

Another object of the invention is to provide a system for and a method of analyzing an ECG, capable of adjusting the base line of ECG time series data upon deriving an ECG attractor from the ECG time series data and thereby achieving the derivation of the attractor rapidly and accurately.

In accordance with one aspect, the present invention provides a method for analyzing an electrocardiogram, including the steps of detecting an electrocardiogram signal from an examinee and extracting electrocardiogram time series data from the detected electrocardiogram signal, executing a base line adjustment for the extracted electrocardiogram time series data, reconstructing an electrocardiogram attractor of the examinee on the basis of the base line-adjusted electrocardiogram time series data, extracting a correlation dimension value on the basis of the reconstructed electrocardiogram attractor, and comparing the reconstructed electrocardiogram attractor and the extracted correlation dimension value respectively with a variety of electrocardiogram attractors previously derived and a variety of correlation dimension values previously derived and diagnosing health and psychological conditions of the examinee on the basis of the result of the comparison.

In accordance with another aspect, the present invention provides an electrocardiogram analyzing system comprising, a control unit for controlling all constituting units of the system, an electrocardiogram data detecting unit for sensing a pulsation of an examinee's heart and thereby outputting electrocardiogram time series data, an analog/digital-converting unit for converting the electrocardiogram time series data outputted from the electrocardiogram data detecting unit, and appropriately extracting digital data required for an attractor reconstruction from the converted electrocardiogram time series data under a control of the control unit, a base line adjusting unit for executing a base line filtering for the extracted electrocardiogram time series data, an attractor reconstructing unit for reconstructing an electrocardiogram attractor of the examinee on the basis of the base line-filtered electrocardiogram time series data, and a diagnosing unit for comparing the reconstructed electrocardiogram attractor with a variety of electrocardiogram attractors experimentally obtained and determining health and psychological conditions of the examinee on the basis of the result of the comparison.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Other objects and aspects of the invention will become apparent from the following description of embodiments with reference to the accompanying drawings in which.

DETAILED DESCRIPTION OF THE PREFERRED EMBODIMENTS

Figure 5:
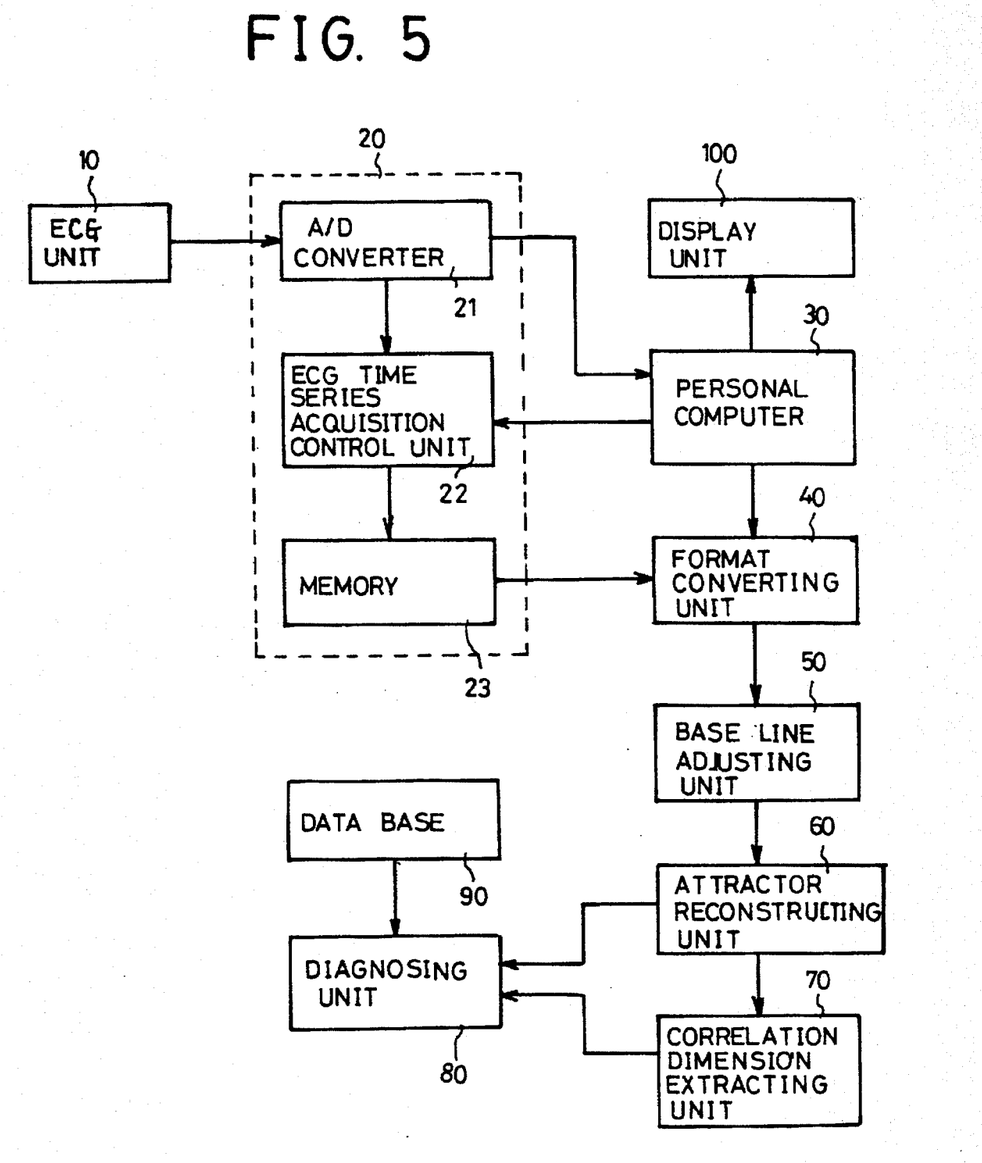
FIG. 5 is a block diagram illustrating an ECG analyzing system in accordance with the present invention.

Referring to FIG. 5, there is illustrated an ECG analyzing system in accordance with the present invention. As shown in FIG. 5, the ECG analyzing system includes an ECG unit 10 serving as a data detecting unit for sensing the pulsation of the heart of an examinee, converting the sensed pulsation in the form of voltage and thereby outputting ECG time series data. A data acquiring board 20 is coupled to the output of the ECG unit 10. The data acquiring board 20 serves as a data processing unit for analog/digital (A/D) converting the ECG time series data outputted from the ECG unit 10, appropriately extracting data required for an attractor reconstruction from the A/D converted ECG time series data, and storing the extracted data in a memory which is denoted by the reference numeral 23. The ECG analyzing system also includes a personal computer 30 serving as a control unit for performing a control to display the ECG time series data outputted from the data acquiring board 20 in a real time and a control to appropriately extract the data required for the attractor reconstruction from the A/D converted ECG time series data. The data acquiring board 20 includes an A/D converter 21 adapted to convert the analog ECG time series data outputted from the ECG unit 10 into digital data and an ECG time series acquisition controller 22 adapted to receive the digital ECG time series data from the A/D converter 21 and appropriately extract data required for the attractor reconstruction from the received data. The memory 23, which constitutes a part of the data acquiring board 20, receives the extracted data from the ECG time series acquisition controller 22. The output data from the A/D converter 21 is also sent to the personal computer 30. The ECG analyzing system further includes a format converting unit 40 for converting the ECG time series data for the attractor reconstruction outputted from the data acquiring board 20 into those compatible with the format of a program to be executed under control of the personal computer 30, a base line adjusting unit 50 for performing a base line filtering for the ECG time series data outputted from the format converting unit 40 such that the base line of the ECG time series data is aligned with a center line, an attractor reconstructing unit 60 for reconstructing an ECG attractor on the basis of the ECG time series data subjected to the base line filtered in the base line adjusting unit 50, and a correlation dimension extracting unit 70 for deriving the correlation dimension of the ECG data on the basis of the attractor outputted from the attractor reconstructing unit 60. A diagnosing unit 80 is coupled to both the attractor reconstructing unit 60 and the correlation dimension extracting unit 70. The diagnosing unit 80 serves to receive the reconstructed ECG attractor from the attractor reconstructing unit 60 and the extracted correlation dimension value from the correlation dimension extracting unit 70 and determine the examinee's health condition from the received data on the basis of ECG attractors and correlation dimension values stored in a data base 90 which constitutes a part of the ECG analyzing system. The data base 90 stores therein a variety of ECG attractors experimentally derived and a variety of correlation dimension values experimentally derived. There is also provided a display unit 100 which serves to display the ECG data in a real time under a control of the personal computer 30.

Operation of the ECG analyzing system in accordance with the present invention will now be described.

ECG signals generated by the pulsation of the heart are chaos signals. Although such chaos signals looks to be random, they have actually a system determined by a complex law of dynamics. When the trajectory of the reconstructed attractor of each chaos signal is plotted in a state space (topological space), it forms a unique topology, as mentioned above. Each chaos signal also has a unique correlation dimension value.

Once an input instrument (not shown) of the ECG unit 10, which is a sensor for sensing the pulsation of the examinee's heart, comes into contact with an appropriate body part of the examinee, the ECG unit 10 generates an infrared ray having the wavelength of about 940 nm which, in turn, reach a capillary vessel of the examinee's body part being in contact with the input instrument. Due to the infrared ray, a variation in volume occurs in the capillary vessel. This volume variation results in a generation of a reflecting light indicative of the amount of oxidized hemoglobin. The reflecting light is received in the ECG unit 10 which, in turn, converts the received light in the form of voltage. That is, the ECG unit 10 generates an ECG time series signal obtained by converting the heart pulsation signal in the form of voltage. The ECG unit 10 amplifies the ECG time series signal to a desired level and then outputs it to the data acquiring board 20.

The A/D converter 21 of the data acquiring board 20 converts the analog ECG time series signal outputted from the ECG unit 10 into a digital signal which is, in turn, sent to both the ECG time series acquisition controller 22 and the personal computer 30. Upon receiving the digital signal, the personal computer 30 operates to execute a control to display the ECG time series data in a real time on the display unit 100. Under a control of the personal computer 30, the ECG time series acquisition controller extract appropriately data required for an attractor reconstruction from the ECG time series data received from the A/D converter 21 and then stores the extracted data in the memory 23. Preferably, the ECG frequency used in the data acquiring board 20 is set to be 900 Hz. However, the user may select softwarily other ECG frequency within the range of from 60 to 900 Hz. The number of data required for the attractor reconstruction is about 15,000. Subsequently, the format converting unit 40 receives the ECG time series data from the memory 23 and then formats the received data into those compatible with the characteristics of a program to be executed under a control of the personal computer 30. The format converting unit 40 sends the formatted data to the base line adjusting unit 50.

Figure 6A:
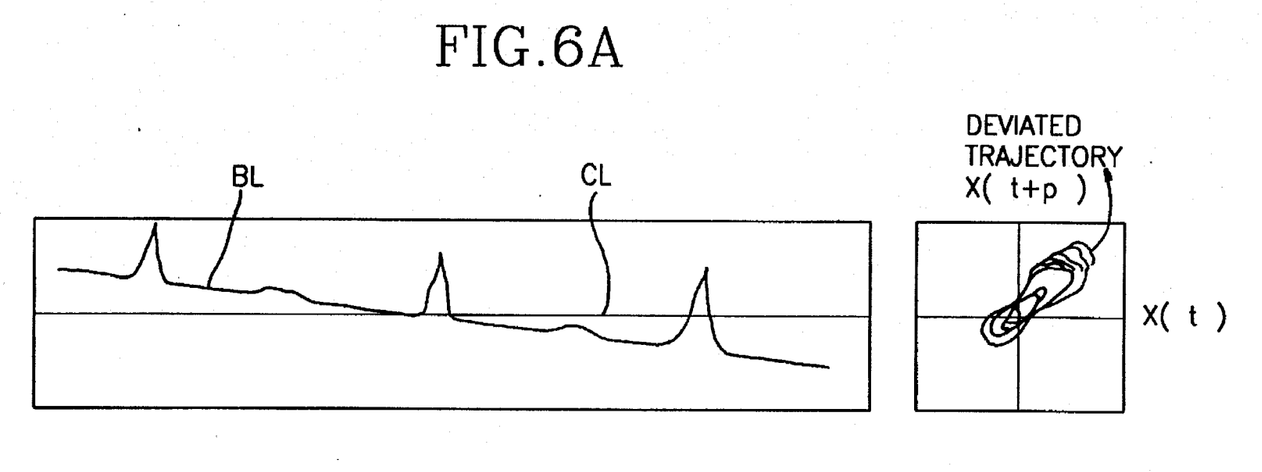
FIGS. 6A and 6B are diagrams for comparing ECG time series data and a reconstructed attractor prior to a base line filtering with those after the base line filtering, respectively.

Meanwhile, the ECG time series data of the examinee displayed on the display unit 100 have a base line not parallel to the center line CL, but with an upper or lower deviation from the center line CL, as shown in FIG. 6A. Such a phenomenon has been known as being caused by factors such as examinee's activity conditions or examinee's psychological conditions. If an attractor reconstruction for ECG time series is carried out based on the data under the above condition, points plotted in a topological space have different references, respectively. As a result, the trajectory of the reconstructed attractor has deviated portions, as shown in FIG. 6A. Such an attractor coincides hardly with the correct attractor of the examinee. For this reason, a normal person's attractor may be misrecognized as that of an abnormal person. By the base line adjusting unit 50, therefore, a base line adjustment should be executed for the ECG time series data outputted from the format converting unit 40. Of course, the attractor reconstruction may be achieved without the base line adjustment. In this case, however, there is a problem that the time taken for the health diagnosis is lengthened because the health diagnosis can not begin until the examinee becomes comfortable. Furthermore, the ECG time series data includes inevitably more or less variation even under the condition that the examinee is comfortable. In order to reconstruct an accurate ECG attractor, therefore, a base line filtering for achieving the base line adjustment is necessarily required.

Figure 7A:
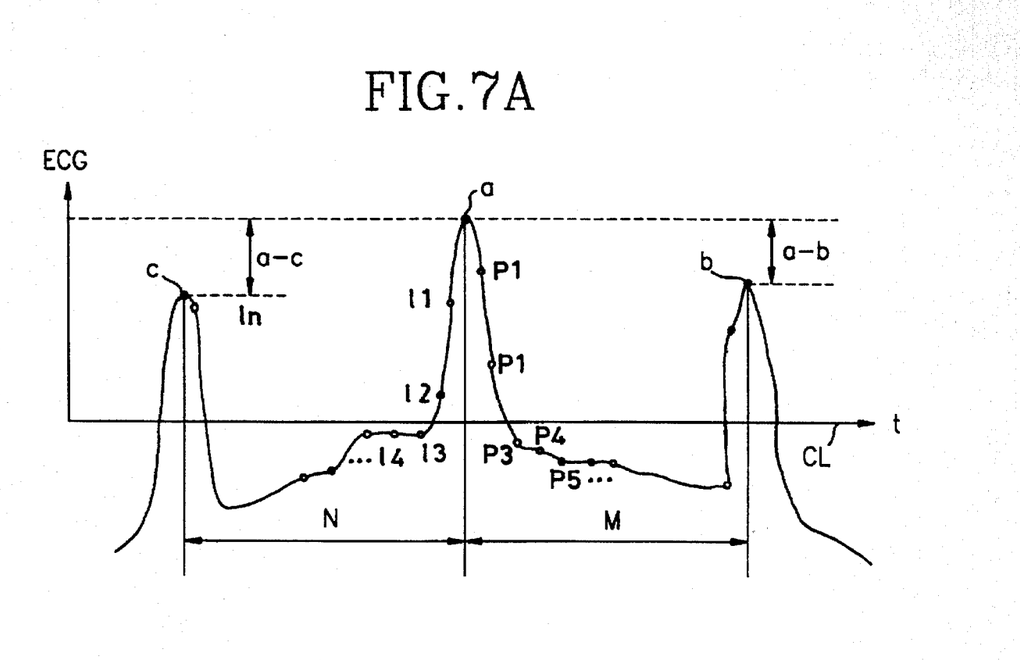
FIGS. 7A and 7B are diagrams respectively for explaining the base line filtering.
Figure 7B:
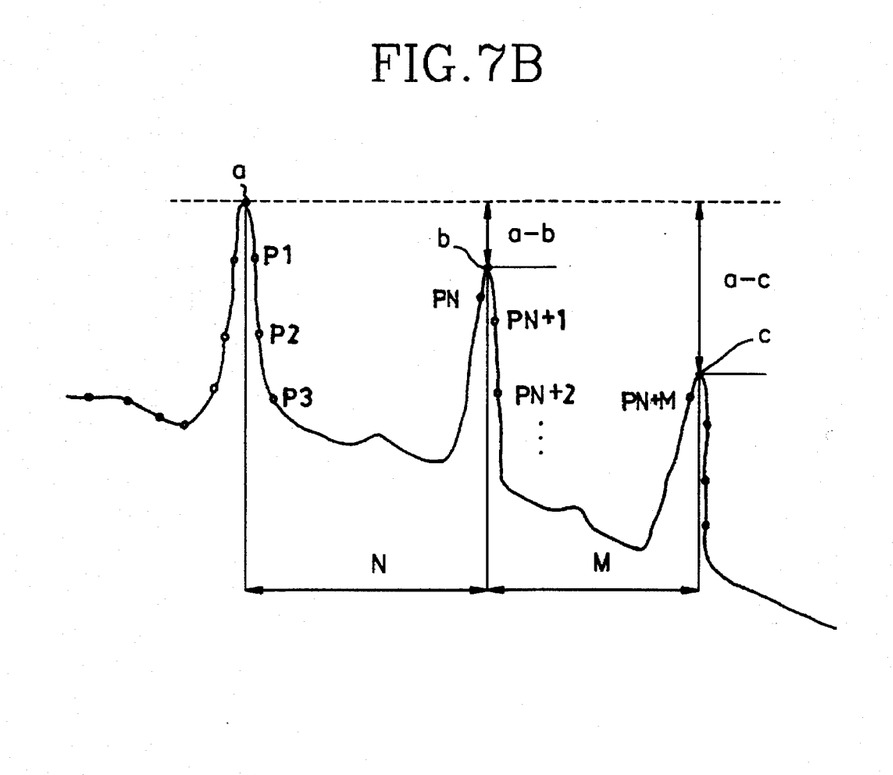

The base line filtering is carried out, as shown in FIGS. 7A and 7B, in accordance with the following method:

First, finding a global peak point a from the extracted ECG time series data;

Second, setting the global peak point a as a reference point for the base line adjustment;

Third, finding local peak points b, c, ..., a part of which follows the global peak point a while the other part preceding the global peak point a as shown in FIG. 7A or all of which follow the global peak point a as shown in FIG. 7B;

Fourth, deriving differences a–b, a–c, ... of respective local peak points b, c, ... from the global peak point a and calculating numbers of data N, M, ... present between respective local peak points b, c, ... and the global peak point a; and Fifth, adjusting the ECG time series data using the values obtained at the fourth step.

At the fifth step, an adjusted value for each data is derived by deriving the difference between the global peak point and the local peak point associated with the data to be adjusted, finding the processing order number of the data to be adjusted between the global peak point and the associated local peak point, multiplying the processing order number of the data by the peak point difference, dividing the resultant value obtained after the multiplication by the number of data present between the global peak point and the associated local peak point, and adding the resultant value obtained after the division to an original value of the data to be adjusted.

For example, where a local peak point b follows the global peak point a while another local peak point c precedes the global peak point a, as shown in FIG. 7A, adjusted values of data are derived respectively using the following equations:

$$l_{1\underline{AV}} = l_{1\underline{OV}} + (a-c) \times \frac{1}{N}, \quad P_{1\underline{AV}} = P_{1\underline{OV}} + (a-b) \times \frac{1}{M},$$

$$l_{2\underline{AV}} = l_{2\underline{OV}} + (a-c) \times \frac{2}{N}, \quad P_{2\underline{AV}} = P_{2\underline{OV}} + (a-b) \times \frac{2}{M},$$

$$l_{3\underline{AV}} = l_{3\underline{OV}} + (a-c) \times \frac{3}{N}, \quad P_{3\underline{AV}} = P_{3\underline{OV}} + (a-b) \times \frac{3}{M},$$

$$\vdots$$

$$l_{n\underline{AV}} = l_{n\underline{OV}} + (a-c) \times \frac{N}{N}, \quad P_{m\underline{AV}} = P_{m\underline{OV}} + (a-b) \times \frac{M}{M}$$

where, l represents the value of data preceding the global peak point a, P represents the value of data following the global peak point a, AV represents the adjusted value of data, and OV represents the original value of data.

Where two local peak points b and c follow the global peak point a, as shown in FIG. 7B, adjusted values are derived respectively using the following equations:

$$P_{1\underline{AV}} = P_{1\underline{OV}} + (a-c) \times \frac{1}{N},$$

$$P_{2\underline{AV}} = P_{2\underline{OV}} + (a-c) \times \frac{2}{N},$$

$$\vdots$$

$$P_{N\underline{AV}} = P_{N\underline{OV}} + (a-c) \times \frac{N}{N},$$

$$P_{N+1\underline{AV}} = P_{N+1\underline{OV}} + (a-c) \times \frac{N+1}{N+M},$$

$$\vdots$$

$$P_{N+M\underline{AV}} = P_{N+M\underline{OV}} + (a-c) \times \frac{N+M}{N+M}$$

Figure 6B:
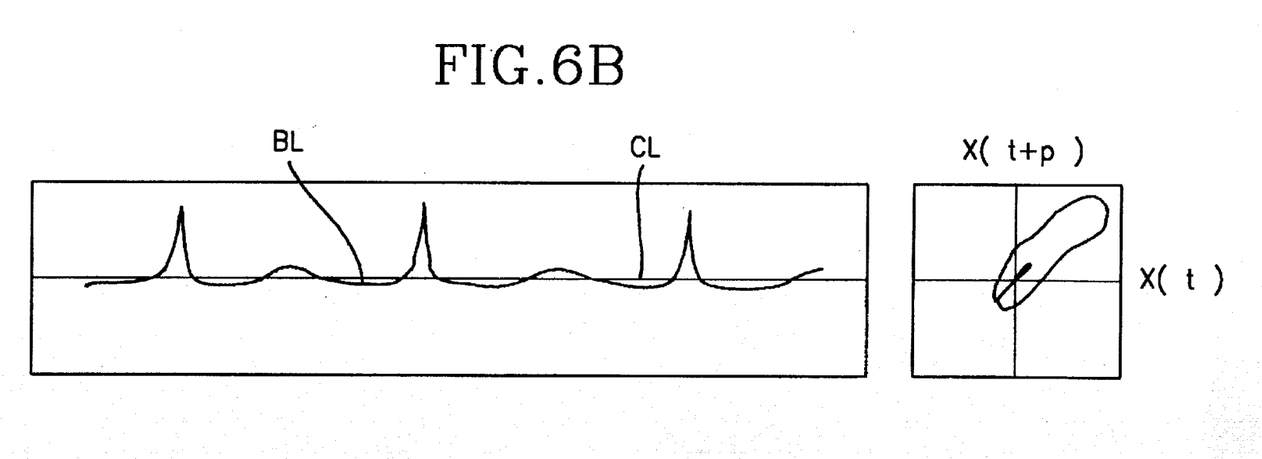

After being subjected to the above processing procedure, the ECG time series data shown in FIG. 6A are adjusted so that their base line BL is horizontally aligned with the center line CL, as shown in FIG. 6B.

The ECG time series data adjusted in the base line adjusting unit 50 is sent to the attractor reconstructing unit 60. Upon receiving the adjusted ECG time series data, the attractor reconstructing unit 60 reconstructs the attractor of the examinee on the basis of the received data, as shown in FIG. 6B. The reconstructed attractor from the attractor reconstructing unit 60 is sent to the diagnosing unit 80 which, in turn, compares the received attractor with a variety of attractors stored in the data base 90, thereby determining the examinee's health condition.

Figure 8A:
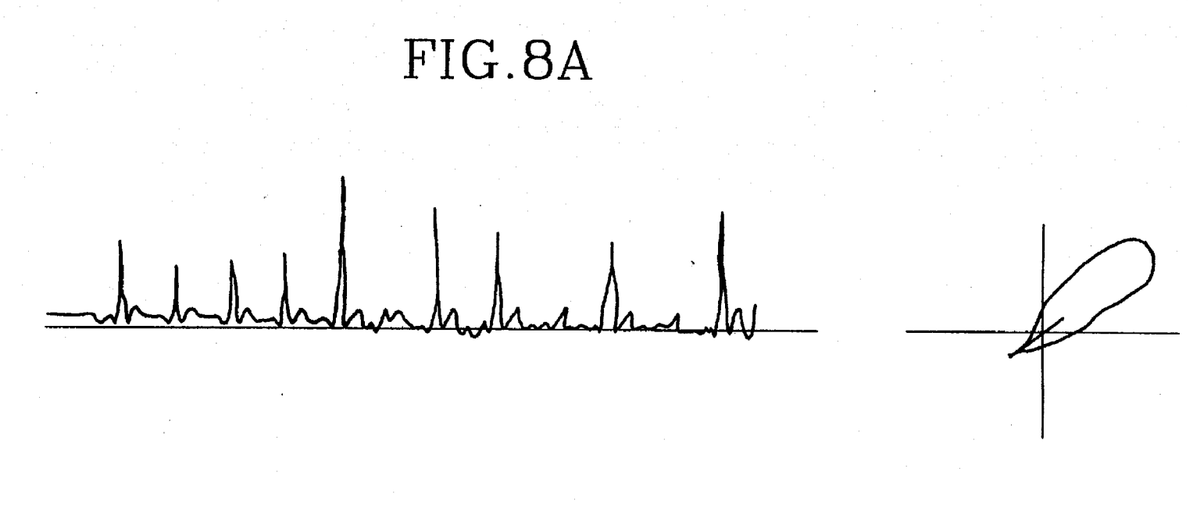
FIGS. 8A and 8B are diagrams of time series data and reconstructed attractors in the case of a normal heart pulsation and in the case of an abnormal heart pulsation, respectively.
Figure 8B:
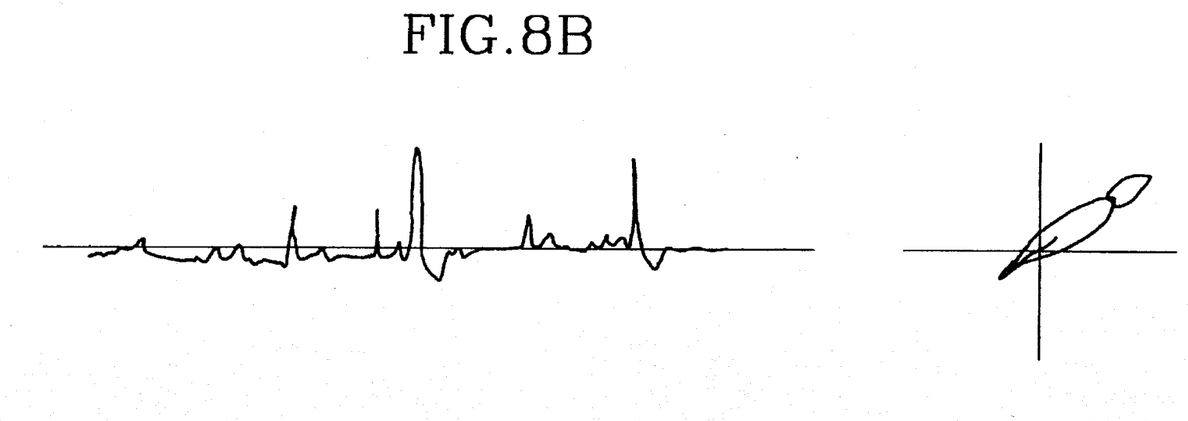

FIG. 8A shows ECG time series data generated in the case of a normal pulsation of the heart and an attractor reconstructed on the basis of such normal ECG time series data whereas FIG. 8A shows ECG time series data generated in the case of an abnormal pulsation of the heart and an attractor reconstructed on the basis of such abnormal ECG time series data. In the case of the abnormal pulsation, the reconstructed attractor has a topology that a protrusion such as lug is protruded from the upper right end of the attractor, as shown in FIG. 8B. In the opinion of doctors, such a phenomenon is exhibited in a patient developing symptoms of arrhythmia.

On the other hand, the correlation dimension extracting unit 70 extracts a correlation dimension using different embedding dimensions through the procedure described in conjunction with FIGS. 3A and 3B and FIGS. 4A to 4C. It is known that the correlation dimension of about 3.xx is obtained in the case of persons exhibiting a normal heart pulsation although the value may be varied more or less for individuals. The correlation dimension value derived as above is then sent to the diagnosing unit 80. Upon receiving the correlation dimension value, the diagnosing unit 80 compares the received value with a variety of experimentally derived correlation dimension values stored in the data base 90, thereby diagnosing the examinee's health and psychological conditions. Meanwhile, an accurate functional relation between the correlation dimension and the health and psychological conditions is the subject to be continuously studied even in future.

As apparent from the above description, the present invention provides a system for and a method of analyzing an ECG, capable of reconstructing an ECG attractor on the basis of ECG time series data generated by the pulsation of the heart by utilizing the chaos principle, deriving a correlation dimension on the basis of the ECG attractor and thereby accurately determining the examinee's health and psychological conditions from the reconstructed ECG attractor and correlation dimension.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for analyzing an electrocardiogram, comprising the steps of:
   detecting an electrocardiogram signal from an examinee and extracting electrocardiogram time series data from the detected electrocardiogram signal;
   executing a base line adjustment for the extracted electrocardiogram time series data;
   reconstructing an electrocardiogram attractor of the examinee on the basis of the base line-adjusted electrocardiogram time series data; and
   comparing the reconstructed electrocardiogram attractor with a variety of electrocardiogram attractors previously derived and diagnosing health and psychological conditions of the examinee on the basis of the result of the comparison.

2. A method in accordance with claim 1, wherein the step of executing the base line adjustment includes the steps of:
   deriving a difference between a global peak point and a local peak point both present in the electrocardiogram time series data, and
   finding a processing order number of the time series data to be adjusted from data values present between the global peak point and the local peak point.

3. A method in accordance with claim 2, wherein the step of executing the base line adjustment further includes the steps of:
   multiplying the processing order number by the peak point difference,
   dividing the resultant value obtained from the multiplication by the total number of data values present between the global peak point and the local peak point, and
   adding the resultant value obtained from the division to an original value of the time series data to be adjusted.

4. A method in accordance with claim 1, wherein the step of detecting the electrocardiogram signal includes the steps of:
   converting the electrocardiogram signal into a digital electrocardiogram signal,
   extracting the electrocardiogram time series data from the digital electrocardiogram signal,
   storing the extracted electrocardiogram time series data in a memory, and
   formatting the extracted electrocardiogram time series data for the base line adjustment.

5. A method for analyzing an electrocardiogram, comprising the steps of:
   detecting an electrocardiogram signal from an examinee and extracting electrocardiogram time series data from the detected electrocardiogram signal;
   executing a base line adjustment for the extracted electrocardiogram time series data;
   reconstructing an electrocardiogram attractor of the examinee on the basis of the base line-adjusted electrocardiogram time series data;
   extracting a correlation dimenions value on the basis of the reconstructed electrocardiogram attractor; and
   comparing the reconstructed electrocardiogram attractor and the extracted correlation dimension value respectively with a variety of electrocardiogram attractors previously derived and a variety of correlation dimension values previously derived and diagnosing health and psychological conditions of the examinee on the basis of the result of the comparison.

6. A method in accordance with claim 5, wherein the step of executing the base line adjustment includes the steps of:
   deriving a difference between a global peak point and a local peak point both present in the electrocardiogram time series data;
   finding a processing order number of the time series data to be adjusted from data values present between the global peak point and the local peak point and multiplying the processing order number of the data by the peak point difference;
   dividing the resultant value obtained from the multiplication by the total number of data values present between the global peak point and the local peak point; and
   adding the resultant value obtained from the division to an original value of the time series data to be adjusted.

7. A method in accordance with claim 5, wherein the step of detecting the electrocardiogram signal includes the steps of:
   converting the electrocardiogram signal into a digital electrocardiogram signal, extracting the electrocardiogram time series data from the digital electrocardiogram signal, storing the extracted electrocardiogram time series data in a memory, and formatting the extracted electrocardiogram time series data for the base line adjustment.

8. An electrocardiogram analyzing system comprising:

a control unit for controlling all constituting units of the system;

an electrocardiogram data detecting unit for sensing a pulsation of an examinee's heart and thereby outputting electrocardiogram time series data;

an analog/digital-converting unit for converting the electrocardiogram time series data outputted from the electrocardiogram data detecting unit, and appropriately extracting digital data required for an attractor reconstruction from the converted electrocardiogram time series data under control of the control unit;

a base line adjusting unit for executing a base line filtering for the extracted electrocardiogram time series data;

an attractor reconstructing unit for reconstructing an electrocardiogram attractor of the examinee on the basis of the base line-filtered electrocardiogram time series data; and a diagnosing unit for comparing the reconstructed electrocardiogram attractor with a variety of electrocardiogram attractors experimentally obtained and determining health and psychological conditions of the examinee on the basis of the result of the comparison.

9. An electrocardiogram analyzing system in accordance with claim 8, further comprising:

a correlation dimension extracting unit for deriving a correlation dimension value on the basis of the reconstructed attractor outputted from the attractor reconstructing unit and sending the correlation dimension value to the diagnosing unit.

10. An electrocardiogram analyzing system in accordance with claim 8, wherein the base line adjusting unit drives a difference between a global peak point and a local peak point both present in the extracted electrocardiogram time series data, finds a processing order number of the time series data to be adjusted from data values present between the global peak point and the local peak point, multiplies the processing order number of the data by the peak point difference, divides the resultant value obtained from the multiplication by the total number of data values present between the global peak point and the local peak point, and adds the resultant value obtained from the division to an original value of the time series data to be adjusted.

11. An electrocardiogram analyzing system in accordance with claim 8, further comprising:

a data base unit for storing the variety of electrocardiogram attractors which are experimentally obtained.

12. An electrocardiogram analyzing system comprising:

detecting means for detecting an electrocardiogram signal from an examinee and extracting electrocardiogram time series data from the detected electrocardiogram signal;

executing means for executing a base line adjustment for the extracted electrocardiogram time series data;

reconstructing means for reconstructing an electrocardiogram attractor of the examinee on the basis of the base line adjusted electrocardiogram time series data; and comparing means for comparing the reconstructed electrocardiogram attractor with a variety of electrocardiogram attractors previously derived and diagnosing health and psychological conditions of the examinee on the basis of the result of the comparison.

13. A system in accordance with claim 12, further comprising:

extracting means for extracting a correlation dimension value on the basis of the reconstructed electrocardiogram attractor, and said comparing means comparing the extracted correlation dimension value with a variety of correlation dimension values previously derived and diagnosing health and psychological conditions of the examinee on the basis of the result of the correlation dimension value comparison.

14. An electrocardiogram analyzing system in accordance with claim 12, wherein the executing means drives a difference between a global peak point and a local peak point both present in the extracted electrocardiogram time series data, finds a processing order number of the time series data to be adjusted from data values present between the global peak point and the local peak point, multiplies the processing order number of the data by the peak point difference, divides the resultant value obtained from the multiplication by the total number of data values present between the global peak point and the local peak point, and adds the resultant value obtained from the division to an original value of the time series data to be adjusted.

15. An electrocardiogram analyzing system in accordance with claim 12, further comprising:

storing means for storing the variety of electrocardiogram attractors which are experimentally obtained.

16. An electrocardiogram analyzing system in accordance with claim 12, wherein the detecting means converts the electrocardiogram signal into a digital electrocardiogram signal, extracts the electrocardiogram time series data from the digital electrocardiogram signal, stores the extracted electrocardiogram time series data into a memory, and formats the extracted electrocardiogram time series data for the base line adjustment.

* * * * *